(12) United States Patent
Kuhn

(10) Patent No.: US 6,840,486 B2
(45) Date of Patent: Jan. 11, 2005

(54) SUPPORT FOR SUPPORTING AT LEAST ONE DEVICE

(75) Inventor: Peter Kuhn, Munich (DE)

(73) Assignee: Mavig GmbH, Munich (DE)

( * ) Notice: Subject to any disclaimer, the term of this patent is extended or adjusted under 35 U.S.C. 154(b) by 0 days.

(21) Appl. No.: 10/344,023

(22) PCT Filed: Jun. 25, 2001

(86) PCT No.: PCT/EP01/07161
§ 371 (c)(1), (2), (4) Date: Feb. 6, 2003

(87) PCT Pub. No.: WO02/14733
PCT Pub. Date: Feb. 21, 2002

(65) Prior Publication Data
US 2004/0026588 A1 Feb. 12, 2004

(30) Foreign Application Priority Data
Aug. 17, 2000 (DE) .......................... 100 40 343

(51) Int. Cl.⁷ ................................. A47H 1/10
(52) U.S. Cl. .................... 248/317; 248/276.1
(58) Field of Search ............... 248/317, 276.1, 248/278.1, 296.1, 279.1, 280.1, 288.3, 481, 181.1, 343, 921

(56) References Cited

U.S. PATENT DOCUMENTS

| | | | |
|---|---|---|---|
| 4,365,561 A | 12/1982 | Tellier et al. | 108/7 |
| 4,516,751 A | 5/1985 | Westbrook | 248/279.1 |
| 5,052,036 A * | 9/1991 | Grady | 378/197 |
| 5,483,572 A * | 1/1996 | Hoornaert et al. | 378/156 |
| 5,709,360 A * | 1/1998 | Rosen | 248/278.1 |
| 6,315,259 B1 * | 11/2001 | Kolb | 248/276.1 |
| 6,325,537 B1 * | 12/2001 | Watanabe | 378/197 |

FOREIGN PATENT DOCUMENTS

| | | |
|---|---|---|
| CH | 653 464 A5 | 12/1985 |
| DE | 862 557 | 11/1952 |
| DE | 94 05 970.5 | 4/1994 |
| EP | 0 862-014 A1 | 9/1998 |

* cited by examiner

Primary Examiner—Ramon O Ramirez
(74) Attorney, Agent, or Firm—Scully, Scott, Murphy & Presser

(57) ABSTRACT

A support (1) for supporting at least one device (2, 3, 4), especially for supporting screen display devices and other medical devices, has a support arm (5) and at least one support device (26) which is at least indirectly connected to said support arm (5). The support device (26) is connected to a support plate (20) in order to receive the device (2, 3, 4). Said support plate can be tilted by means of a regulating mechanism (72) in order to tilt the device (2, 3, 4).

6 Claims, 3 Drawing Sheets

SUPPORT FOR SUPPORTING AT LEAST ONE DEVICE

Figure 1:
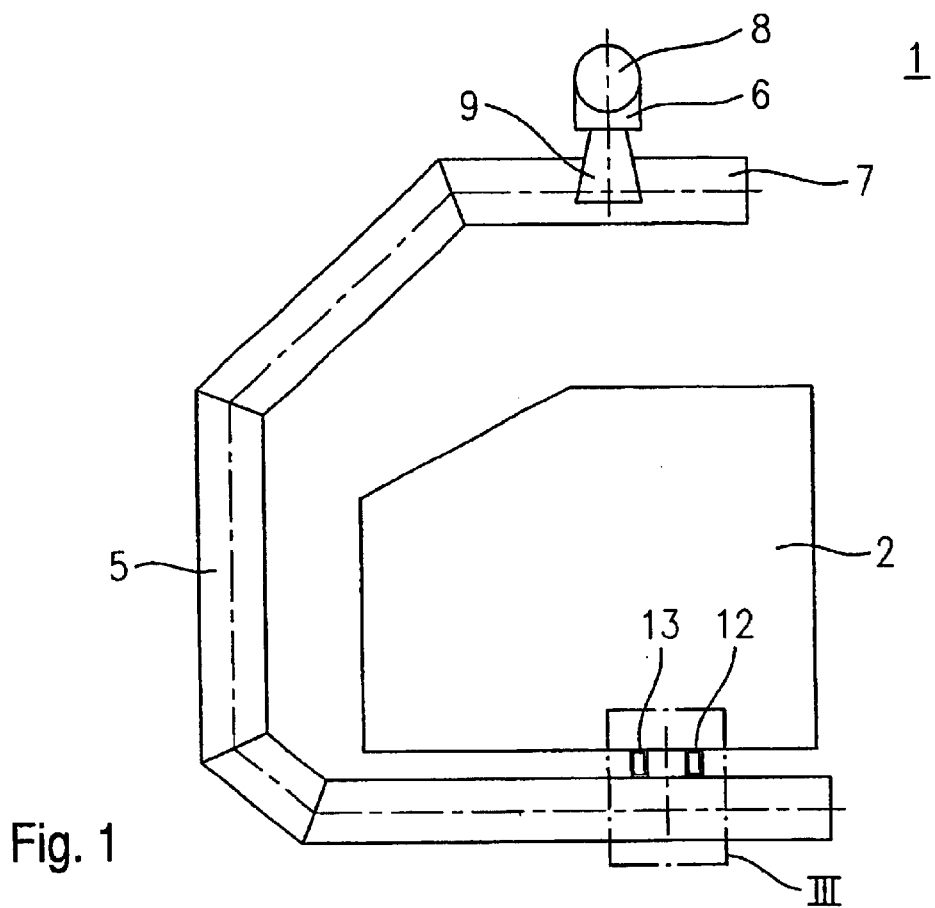

The invention relates to a support for supporting at least one apparatus, in particular for supporting visual display units and other medical devices.

The known supports for supporting apparatuses, in particular for employment in medical facilities, are used for the raised fastening of an apparatus by means of a spring arm to the ceiling of a consulting room or the like. In particular, supports having a C-shaped support arm are known, which are fastened by means of a fastening device to the spring arm. The suspension point, at which the support arm is fastened by means of the fastening device to the spring arm, is in said case predetermined by the apparatuses to be fastened, so that given the desired horizontal alignment of the support arm the centre of gravity of the loaded support arm lies below the suspension point. The said apparatuses are fastened to the support arm by means of a crossmember, which is fastened to the support arm. By virtue of said fastening the inclination of the apparatus relative to the horizontal is determined.

The known support has several drawbacks. As the inclination of the apparatus is fixed in advance, an adaptation of the alignment of the apparatus to the viewing angle of a user, which is necessary e.g. with a visual display unit, is not possible. Furthermore, given use of an apparatus having a different centre-of-gravity distribution and/or of a different weight to the apparatus, to which the support is tuned, the problem arises that the support is swivelled into a position with an inclination other than the desired inclination, so that the inclination of the fastened apparatus is disadvantageous. For example, in the case of a visual display unit the result is then a disadvantageous viewing angle for all and/or for at least most of the users.

A further drawback, which arises particularly when a plurality of apparatuses are supported by the support, is that the position of the apparatus with regard to its vertical axis is fixed in advance relative to the support. Particularly given a plurality of apparatuses, it is desirable for the latter to be rotated relative to one another to facilitate access to the apparatuses, e.g. for operating a switch, and to optimize an advantageous direction of viewing each of the apparatuses, e.g. for reading off information.

The underlying object of the invention is therefore to provide a support, with which the orientation of an apparatus supported by the support relative to the support and, in particular, the inclination of the apparatus is adjustable.

The support according to the invention has the advantage that the inclination of the apparatus supported by the support is adjustable. As a result, starting e.g. from a horizontal orientation of the apparatus a rotation out of the horizontal may be effected in order to incline the apparatus. The alignment of the apparatus may therefore be adapted to a user in order to enable e.g. advantageous access or an adaptation to the viewing direction of the user.

In an advantageous manner the support plate is mounted rotatably in a first bearing of the support device, wherein the first bearing defines the axis of rotation, about which the support plate is rotated for the purpose of inclination. In said case, it is moreover advantageous that the support plate is further mounted in a second bearing of the support device, wherein the second bearing is three-dimensionally adjustable by means of the control element for inclining the support plate. The first bearing defines an axis of rotation, which is disposed in a stationary manner relative to the support device and about which the support plate is rotatable for the purpose of inclination. The axis of rotation may in said case also lie outside of the support plate. Given a fixed axis of rotation, there remains for the support plate a further degree of freedom, which consists of rotation about said axis. By means of the second bearing said remaining degree of freedom is also fixed, wherein by adjusting the control element for inclining the support plate a rotation of the support plate about the axis of rotation is effected. The result is therefore an at least substantially play-free bearing arrangement of the support plate by means of the support device, wherein the rotary position of the support plate is fixed in both directions of rotation in relation to the axis of rotation by the bearing arrangement.

In an advantageous manner the second bearing comprises at least one connecting rod, which is connected on the one hand to a bearing element of the support plate and on the other hand to a bearing element of the support device. By virtue of the connecting rod a simple transfer of the adjustment effected by the control element to the support plate is provided, wherein during the adjustment a displacement of the bearing element of the support plate relative to the bearing element of the support device, particularly in a horizontal direction, is compensated.

It is advantageous that the control element adjusts the second bearing in a direction, which is at least substantially at right angles to the support face of the support plate. As a result, the forces generated and acting upon the components of the support, in particular upon the second bearing, may be reduced to the required amount. Furthermore, an advantageous stroke translation of the adjustment of the control element into the inclination of the support plate is effected.

It is advantageous that the control element comprises a crank handle for actuating the control element. The control element may therefore be adjusted quickly, easily and precisely in order to achieve the desired inclination of the apparatus disposed on the support plate.

In an advantageous manner the control element comprises a spindle, which is actuable by means of the crank handle and converts a rotational motion of the crank handle into a stroke for inclining the support plate. In said case, by virtue of the lead of the spindle it is possible to preset the transmission ratio, i.e. the stroke for inclining the support plate for one revolution of the spindle effectable by means of the crank handle, so that, given a small lead of the thread of the spindle, a particularly precise variation and, given a large lead of the spindle, a particularly rapid variation of the inclination of the support plate is achievable. The precision of the adjustment is in said case influenced moreover by the diameter of the circular line, along which the crank of the crank handle is movable upon actuation of the spindle.

In an advantageous manner the support device comprises a third bearing for swivelling the support plate about an axis, which is at least approximately at right angles to the support face of the support plate. Thus, in addition to the inclination of the support plate achievable by means of the first and second bearings, a rotation of the support plate may be enabled by means of the third bearing, thereby enabling a rotation of the apparatus about two axes of rotation at right angles to one another. In said case, it is particularly advantageous that the axis of rotation defined by the third bearing is at least approximately at right angles to the support face of the support plate and/or approximately horizontal. Thus, an ergonomic adaptation of the alignment of the apparatus, in particular an adaptation of the adjusted viewing direction, to a user may be effected.

In said case, it is further advantageous that a braking device is provided for damping the bearing arrangement of the support plate provided by the third bearing. This prevents an inadvertent horizontal swinging from occurring e.g. during a movement of the support or an actuation of the apparatus. Furthermore, by clamping the braking device an arresting of the horizontal swinging of the support plate and/or of the apparatus disposed on the support plate relative to the axis of the third bearing may be effected.

Figure 2:
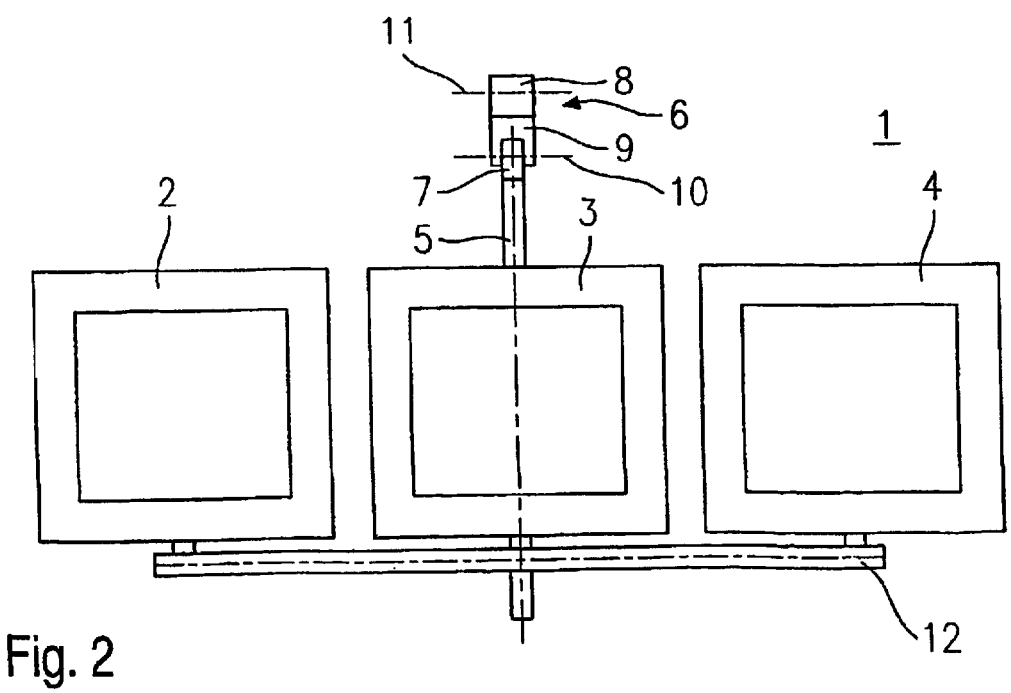
Figure 3:
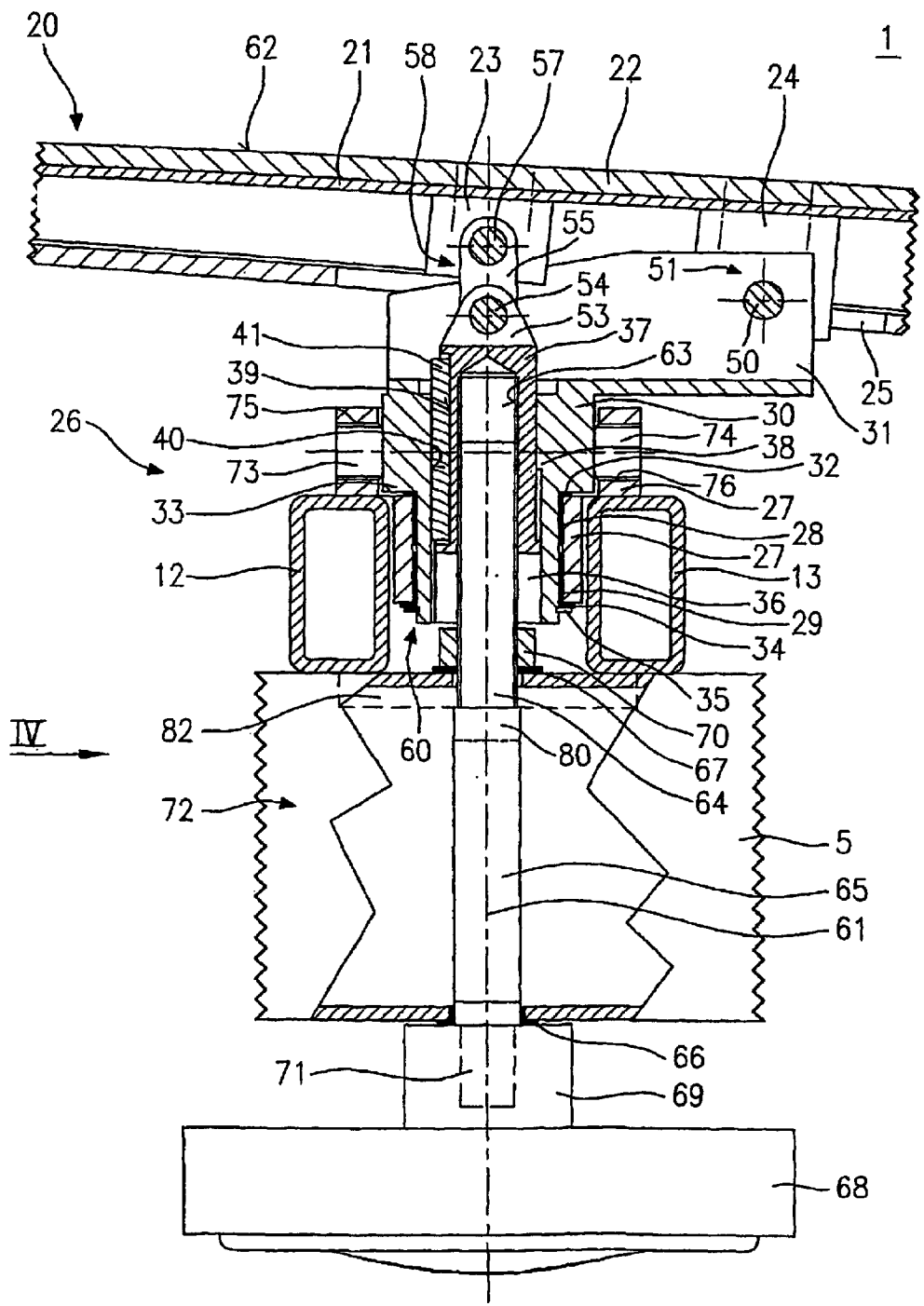
Figure 4:
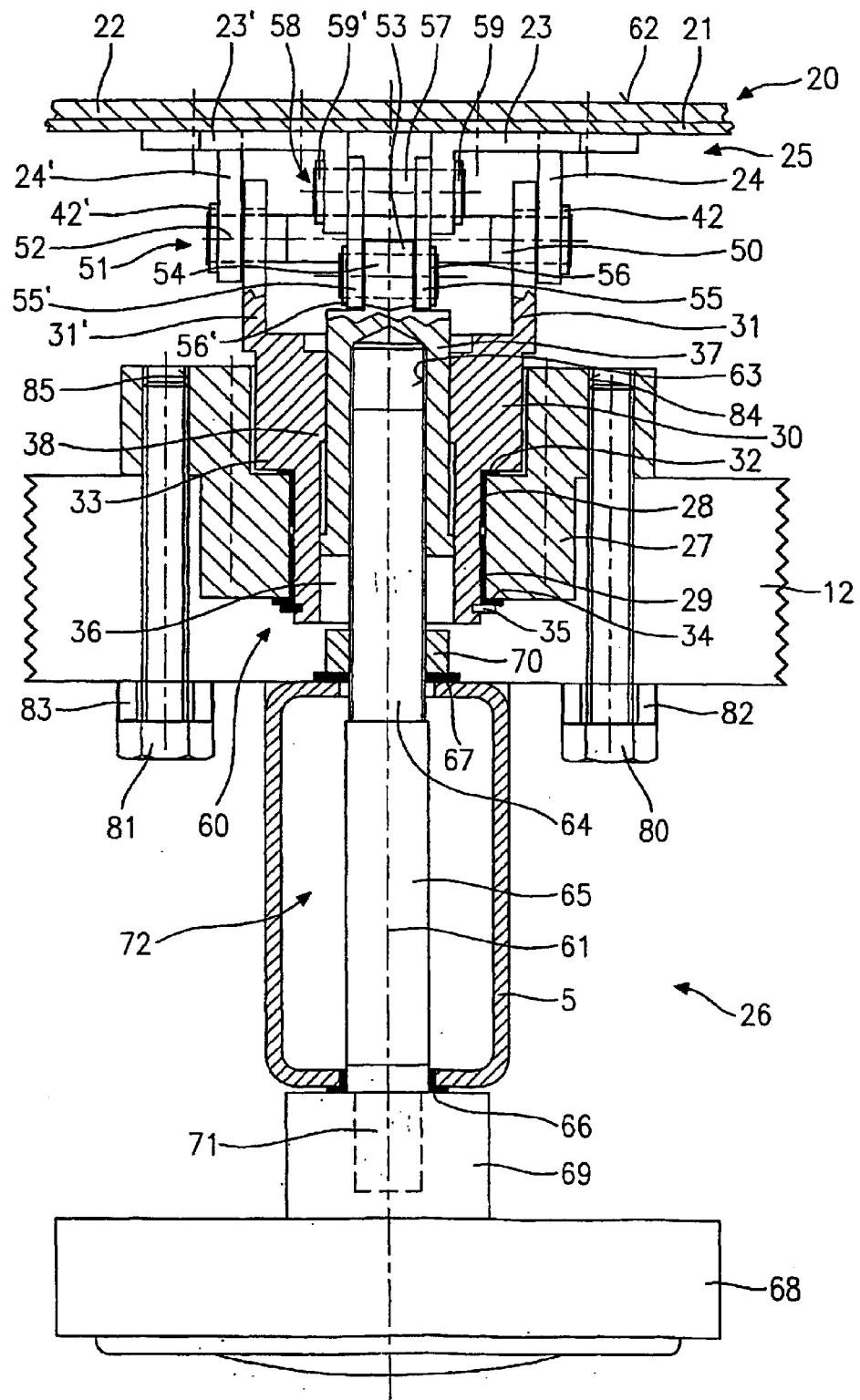

There now follows a detailed description of a preferred embodiment of the invention with reference to the drawings. The drawings show in:

FIG. 1 a side view of a support;

FIG. 2 a front view of the support illustrated in FIG. 1;

FIG. 3 the detail denoted by III in FIG. 1 according to the preferred embodiment of the invention in a part-sectional view; and FIG. 4 the detail of the preferred embodiment illustrated in FIG. 3 in a part-sectional view in the direction denoted by IV in FIG. 3.

FIG. 1 shows the basic structure of a support 1 for supporting apparatuses 2, 3, 4, in particular for supporting visual display units and other medical devices. The support 1 is intended in particular for use in medical facilities, such as surgeries, clinics and operating theatres, in order to provide a raised supporting and/or fastening device for the medical devices and the like. The support 1 according to the invention is however also suitable for other areas of application.

The support 1 comprises a C-shaped support arm 5 and a fastening device 6 connected to the latter, wherein the fastening device 6 is disposed on the top part 7 of the support arm 5. The fastening device 6 comprises an articulated piece 8, at which the support 1 is connectable to a suitable holding device. The holding device may be e.g. a spring arm fastened to the ceiling of the room, in which the support is being used. The fastening device 6 moreover comprises a connecting piece 9, at which the fastening device 6 is connected to the top part 7 of the support arm 5. Said connection may allow, at least within specific limits, a rotation of the support arm 5 about the axis 10 illustrated in FIG. 2 relative to the connecting piece 9 of the fastening device 6, or may alternatively be of a rigid design so as to prevent rotatability relative to the axis 10. At any rate, the support arm 5 is mounted on the articulated piece 8 so as to be rotatable relative to the holding device about the axis 11, which is the axis of rotation of the articulated piece 8, so that the centre of gravity of the support 1 loaded with the apparatuses 2, 3, 4 comes to lie, in terms of its vertical direction, below the axis 11.

The apparatuses 2, 3, 4 are fastened to crossmembers 12, 13 formed from hollow section bodies with a rectangular cross section. The fastening is described in detail below with reference to FIGS. 3 and 4. The crossmembers 12, 13 are connected to the support arm 5, wherein the connection may be a weld joint, screw connection or the like.

FIG. 2 shows a front view of the support 1 illustrated in FIG. 1. Elements, which have already been described, are provided with identical reference characters in FIG. 2 and in all of the other figures, thereby rendering a repeat description superfluous.

FIG. 3 shows the detail, which is denoted by III in FIG. 1, according to a preferred embodiment of the invention. The support 1 has a support plate 20, which comprises a basic body 21 preferably made of metal and a casing body 22 preferably made of plastics material, which encases the basic body 21. The support plate 20 moreover comprises bearing elements 23, 24, which are connected, e.g. by a weld joint, to the basic body 21. The casing body 22 of the support plate 20 has a recess 25, through which the bearing elements 23, 24 are accessible for connecting to a support device 26.

The support device 26 comprises a basic body 27, which is connected to the crossmembers 12, 13. A bearing body 30, which comprises a bearing element 31, is mounted in the basic body 27 of the support device 26 by means of the bearing sleeves 28, 29. The bearing sleeve 28 has a collar 32, which is disposed between the basic body 27 and a projection 33 of the bearing body 30, so that in addition to the radial bearing arrangement by means of the bearing sleeves 28, 29 an axial bearing arrangement is provided. In said case, on the bearing sleeve 29 also a collar 34 is formed, which is provided at least partially between a retaining ring 35 and the basic body 27, so that in cooperation with the bearing sleeve 28 a double-ended axial bearing arrangement is provided. In said case, the bearing body 30 is secured by means of the retaining ring 35, with the result that a fastening of the bearing body 30 by means of the basic body 27 to the crossmembers 12, 13 is provided.

The bearing body 30 has a stepped bore 36, in which a spindle bush 37 is guided, wherein the mobility of the spindle bush 37 in the guide is limited by a stop 38 formed on the bearing body 30. The stepped bore 36 has a slot-like recess 39, lying partially opposite to which is a likewise slot-like recess 40 formed in the bearing body 30. Provided between the bearing body 30 and the spindle bush 37 is a transition piece 41, which engages partially into the slot-like recess 39 of the spindle bush 37 and partially into the slot-like recess 40 of the projection 33, thereby preventing a rotational motion of the spindle bush 37 relative to the bearing body 30. The transition piece 41 may be formed from a spring steel sheet or a metal lamella. As the recess 40 in the bearing body 30 is formed along the entire stepped bore 36 and is open particularly at its ends, the axial displaceability of the spindle bush 37 is not influenced by the described mechanism, which prevents a rotation of the spindle bush 37 relative to the bearing body 30.

The support according to the invention according to the preferred embodiment is described in detail below with additional reference to FIG. 4. FIG. 4 shows the detail, which is illustrated in FIG. 3 and denoted by III in FIG. 1, from the direction denoted by IV in FIG. 3.

Lying opposite the bearing element 31 of the bearing body 30 is a bearing element 31' of the bearing body 30. In a corresponding manner, lying opposite the bearing element 24 of the support plate 20 connected to the basic body 21 of the support plate 20 is the bearing element 24', which is likewise connected to the basic body 21 of the support plate 20. The bearing body 30 is connected at the bearing elements 31, 31' by means of a bearing bolt 50 to the bearing elements 24, 24' of the support plate 20, wherein the bearing bolt 50 is rotatable relative to the bearing elements 24, 24' of the support plate 20 and/or relative to the bearing elements 31, 31' of the bearing body 30. In said case, the bearing bolt 50 is locked against axial displacement by means of the retaining rings 42, 42'.

The bearing elements 31, 31' of the bearing body 30, the bearing elements 24, 24' of the support plate 20 and the bearing pin 50 form a first bearing 51, which defines an axis of rotation 52, which corresponds to the axis of the bearing pin 50 and about which the support plate 20 is rotatable. Thus, the support plate 20 is mounted rotatably in the first bearing 51 of the support device 26, wherein the axis of rotation is provided by the axis of the bearing pin 50.

The spindle bush 37 comprises the bearing element 53, which is connected by means of the bearing pin 54 to the connecting rod 55 and the connecting rod 55', wherein the bearing pin 54 is rotatable relative to the bearing element 53 and/or the connecting rods 55, 55', and the bearing pin 54 is locked against axial displacement by means of the retaining rings 56, 56'. The connecting rods 55, 55' are therefore connected on the one hand by means of the bearing pin 54 to the bearing element 53 of the spindle bush 37 of the support device 26. On the other hand, the connecting rods 55, 55' are connected by means of a rotatable bearing pin 57 to the bearing elements 23, 23', which are connected to the basic body 21 of the support plate 20. The bearing element 53 of the support device 26, the bearing elements 23, 23' of the support plate 20 and the connecting rods 55, 55', which are connected on the one hand by means of the bearing pin 54 to the bearing element 53 of the support device 26 and on the other hand by means of the bearing pin 57 to the bearing elements 23, 23' of the support plate 20, form a second bearing 58 of the support device 26, in which bearing the support plate 20 is mounted in addition to the bearing arrangement in the first bearing 51. In said case, the bearing pin 57 is locked in axial direction by means of the retaining rings 59, 59'.

Furthermore, the bearing body 30 together with the basic body 27, the bearing sleeves 28, 29 and the retaining ring 35 forms a third bearing 60, which is a component part of the support device 26. The third bearing 60 enables a rotatability of the bearing body 30 about an axis 61, so that the support plate 20 is rotatable about the axis 61 in order to swivel the support plate 20. In said case, the axis 61 is oriented at least approximately at right angles to the support face 62 of the support plate 20.

The spindle bush 37 has a threaded bore 63, into which a threaded portion 64 of a spindle 65 engages. The spindle 65 penetrates the support arm 5 and is mounted on the support arm 5 by means of a bearing sleeve 66 and by means of a bearing ring 67. In said case, the spindle 65 is connected to a crank handle 68, which comprises a spacer 69, against which the bearing sleeve 66 is supported. A setting element 70 screwed onto the threaded portion 64 of the spindle 65 is used to set the bearing clearance of the bearing provided by the bearing sleeve 66, the bearing ring 67, the support arm 5 and the spacer 69.

The crank handle 68 is connected at the spacer 69 to a connecting piece 71 of the spindle 65. Instead of the crank handle 68, a different adjusting device may be provided on the connecting piece 71 of the spindle 65.

The spindle 65 together with the spindle bush 37 and the crank handle 68 forms a control element 72, which generates a stroke for adjusting the inclination of the support plate 20, in particular of the support face 62 of the support plate 20. The stroke of the control element 72 is in said case converted by the first bearing 51 and the second bearing 58 into a rotational motion and/or inclination of the support plate 20. By actuating the crank handle 68 the spindle 65 (together with the setting element 70) is rotated about the axis 61 so that, in particular, the threaded portion 64 of the spindle 65 rotates relative to the spindle bush 37 held fast by means of the transition piece 41, thereby producing an adjustment and/or stroke of the spindle bush 37 in an axial direction parallel to the axis 61. The second bearing 58 is therefore adjusted relative to the first bearing 51, wherein the first bearing 51 defines the axis of rotation 52 for a rotation and/or inclination of the support plate 20. Thus, the stroke generated by the control element 72 is converted into a rotation of the support plate 20 about the axis of rotation 52.

The bearing body 30 of the support device 26 is rotatable by means of the third bearing 60 about the axis 61 of the spindle 65, wherein a braking device comprising the braking screws 73, 74 is provided for damping the bearing arrangement provided by the third bearing 60. The braking screws 73, 74 are screwed into threaded bores 75, 76 of the basic body 27, wherein by virtue of the length of thread engagement the frictional force determining the extent of damping is adjustable. For said purpose, a friction insert made of e.g. a rubber compound is advantageously provided on the ends of the braking screws 73, 74 facing the bearing body 30.

The support face 62 is used to support the apparatus 3. In said case, the apparatus 3 may be connected e.g. by screw or clamp connections to the support plate 20. The apparatus 3 may however alternatively be placed, without further connection, onto the support face 62 of the support plate 20. By means of the control element 72 of the support device 26 the inclination of the apparatus 3 relative to the horizontal may be adjusted. The apparatus 3 may moreover be swivelled by means of the support device 26 about the axis 61, which is oriented approximately vertically. The apparatus 3 may therefore be rotated about two axes at least approximately at right angles to one another, namely the axis 61 and the axis of rotation 52.

The basic body 27, for fastening purposes, is screwed firmly to the support arm 5 by means of the fastening screws 80, 81, wherein the fastening screws 80, 81 are supported against fastening plates 82, 83. Said fastening plates 82, 83 lie against the underside of the crossmember 12 and against the underside of the crossmember 13 respectively. The fastening screws 80, 81 in said case extend through recesses in the fastening plates 82, 83 and are disposed between the crossmembers 12, 13 and engage at their ends into threaded bores 84, 85 formed in the basic body 27.

The fastening of the support device 26 to the crossmembers 12, 13, which is described with reference to FIGS. 3 and 4, is preferably provided for the middle position on the crossmembers 12, 13, i.e. for the apparatus 3, because there the support arm 5 is disposed below the crossmembers 12, 13. For the other positions, i.e. for the apparatuses 2, 4, a slightly different fastening is preferably provided. As in said case the support arm 5 no longer applies, instead of the fastening plates 82, 83 a single large fastening plate is used, into which the fastening screws 80, 81 are screwed at the same point as in FIG. 4, wherein the fastening plate at the same time has a recess, through which the spindle 65 extends and in which the bearing sleeve 66 is disposed. By said means, moreover, the distance between the spacer 69 and the threaded portion 64 of the spindle 65 may be considerably reduced.

What is claimed is:

1. Support (1) for supporting at least one apparatus (2, 3, 4), in particular for supporting visual display units and other medical devices, comprising a support arm (5) and at least one support device (26), which is connected at least indirectly to the support arm (5), wherein the support device (26) for receiving the apparatus (2, 3, 4) is connected to a support plate (20), which is inclinable by means of a control element (72) for inclining the apparatus (2, 3, 4), wherein the support plate (20) is mounted rotatably in a first bearing (51) of the support device (26), wherein the first bearing (51) defines the axis of rotation (52), about which the support plate (20) is rotation for the purpose of inclination, and wherein the support plate (20) is further mounted in a second bearing (58) of the support device (26), wherein the second bearing (58) is three-dimensionally adjustable by means of the control element (72) for inclining the support plate (20), characterized in that the second bearing (58) comprises at least one connecting rod (55), which is connected on the one hand to a bearing element (23, 23') of the support plate (20)

and on the other hand to a bearing element (53, 53') of the support device (26).

2. Support according to claim 1, characterized in that the control element (72) adjusts the second bearing (58) in a direction, which is at least substantially at right angles to the support face (62) of the support plate (20).

3. Support according to claim 1, characterized in that the control element (72) comprises a crank handle (68) for actuating the control element (72).

4. Support according to claim 3, characterized in that the control element (72) comprises a spindle (65), which is actuable by means of the crank handle (68) and converts a rotational motion of the crank handle (68) into a stroke for inclining the support plate (20).

5. Support according to claim 1, characterized in that the support device (26) comprises a third bearing (60) for swiveling the support plate (20) about an axis (61), which is at least approximately at right angles to the support face (62) of the support plate (20).

6. Support according to claim 5, characterized in that a braking device (73, 74) is providing for damping the bearing arrangement of the support plate (20) provided by the third bearing (60).

* * * * *